United States Patent
Cao et al.

(10) Patent No.: US 11,131,648 B2
(45) Date of Patent: Sep. 28, 2021

(54) POTENTIOMETRIC SENSOR

(71) Applicant: Energy, United States Department of, Washington, DC (US)

(72) Inventors: Guoping Cao, Idaho Falls, ID (US); Shelly X. Li, Idaho Falls, ID (US); Steven Herrmann, Idaho Falls, ID (US); Brenda Serrano-Rodriguez, Spring Lake, NC (US)

(73) Assignee: U.S. Department of Energy, Washington, DC (US)

( * ) Notice: Subject to any disclaimer, the term of this patent is extended or adjusted under 35 U.S.C. 154(b) by 264 days.

(21) Appl. No.: 16/447,028

(22) Filed: Jun. 20, 2019

(65) Prior Publication Data

US 2020/0400609 A1 Dec. 24, 2020

(51) Int. Cl.
| | |
|---|---|
| *G01N 27/416* | (2006.01) |
| *G01N 27/30* | (2006.01) |
| *G01N 27/403* | (2006.01) |
| *G01N 27/40* | (2006.01) |
| *G01N 33/205* | (2019.01) |

(52) U.S. Cl.
CPC ......... *G01N 27/4161* (2013.01); *G01N 27/30* (2013.01); *G01N 27/301* (2013.01); *G01N 27/40* (2013.01); *G01N 27/403* (2013.01); *G01N 33/205* (2019.01)

(58) Field of Classification Search
CPC ...... G01N 27/30; G01N 27/31; G01N 27/403; G01N 33/205
See application file for complete search history.

(56) References Cited

U.S. PATENT DOCUMENTS

| | | | | |
|---|---|---|---|---|
| 4,645,571 | A * | 2/1987 | Dubreuil ............ | G01N 27/4114 204/422 |
| 5,096,552 | A * | 3/1992 | Fray ................... | G01N 27/4045 205/790 |
| 5,393,400 | A * | 2/1995 | Yamaguchi .......... | G01N 33/205 204/413 |

OTHER PUBLICATIONS

Ipser et al., "Overview: The emf method as a source of experimental thermodynamic data," CALPHAD: Computer Coupling of Phase Diagrams and Thermochemistry 34 (2010) 271-278 (Year: 2010).*
Ionotec description of conductive ceramics downloaded May 6, 2021 from http://www.ionotec.com/conductive-ceramics.html, published 2013.*

* cited by examiner

*Primary Examiner* — Alexander S Noguerola
(74) *Attorney, Agent, or Firm* — Felisa L. Leisinger; Michael J. Dobbs; Brian J. Lally

(57) ABSTRACT

According to one aspect of the invention, a potentiometric sensor having a cathode and an anode. The cathode is configured to provide a summary voltage representative of at least two voltage points. The anode is configured to provide a first voltage. The cathode is in communication with the anode by a first electrolyte forming an open circuit having an open circuit potential. Within the first electrolyte is a concentration of a target ion. The open circuit potential mathematically corresponds to the concentration of the target ion.

16 Claims, 3 Drawing Sheets

POTENTIOMETRIC SENSOR

GOVERNMENT INTERESTS

The United States Government has rights in this invention pursuant to Contract No. DE-AC07-05ID14517 between the U.S. Department of Energy (DOE) and Battelle Energy Alliance.

FIELD OF THE INVENTION

The present invention relates to a potentiometric sensor.

BACKGROUND OF THE INVENTION

The necessity of processing spent nuclear fuel, for either reuse or storage, is growing. Pyroprocessing, where nuclear fuel is dissolved in spent fuel at high temperatures in a molten salt, is used a precursor step to electrorefining, where actinides are removed from the fuel salt. The pyroprocessing of the spent nuclear fuel must be closely monitored to ensure efficient and safe operations are taking place. But, currently the concentration of actinides in the fuel salt is usually conducted by chemical analysis, which is time-consuming, inconvenient and not real-time. Accurate on-line monitoring of actinide concentrations, in particular $UCl_3$ and $PuCl_3$, in molten salts for electrorefining is highly desirable for electrochemical operations, material accountancy, and materials safeguards. Therefore, there is a need for a sensor that provides instantaneous and efficient on-line monitoring of $UCl_3$ in molten salts.

SUMMARY OF THE INVENTION

According to one aspect of the invention, a potentiometric sensor having a cathode and an anode. The cathode is configured to provide a summary voltage representative of at least two voltage points. The anode is configured to provide a first voltage. The cathode is in communication with the anode by a first electrolyte forming an open circuit having an open circuit potential. Within the first electrolyte is a concentration of a target ion. The open circuit potential mathematically corresponds to the concentration of the target ion.

BRIEF DESCRIPTION OF THE DRAWINGS

Embodiments of the present invention are illustrated in the accompanying figures where.

DETAILED DESCRIPTION OF THE INVENTION

The following detailed description provides illustrations for embodiments of the present invention. Each example is provided by way of explanation of the present invention, not limitation of the present invention. Those skilled in the art will recognize that other embodiments for carrying out or practicing the present invention are also possible. Therefore, it is intended that the present invention covers such modifications and variations as come within the scope of the appended claims and their equivalents.

Figure 1:
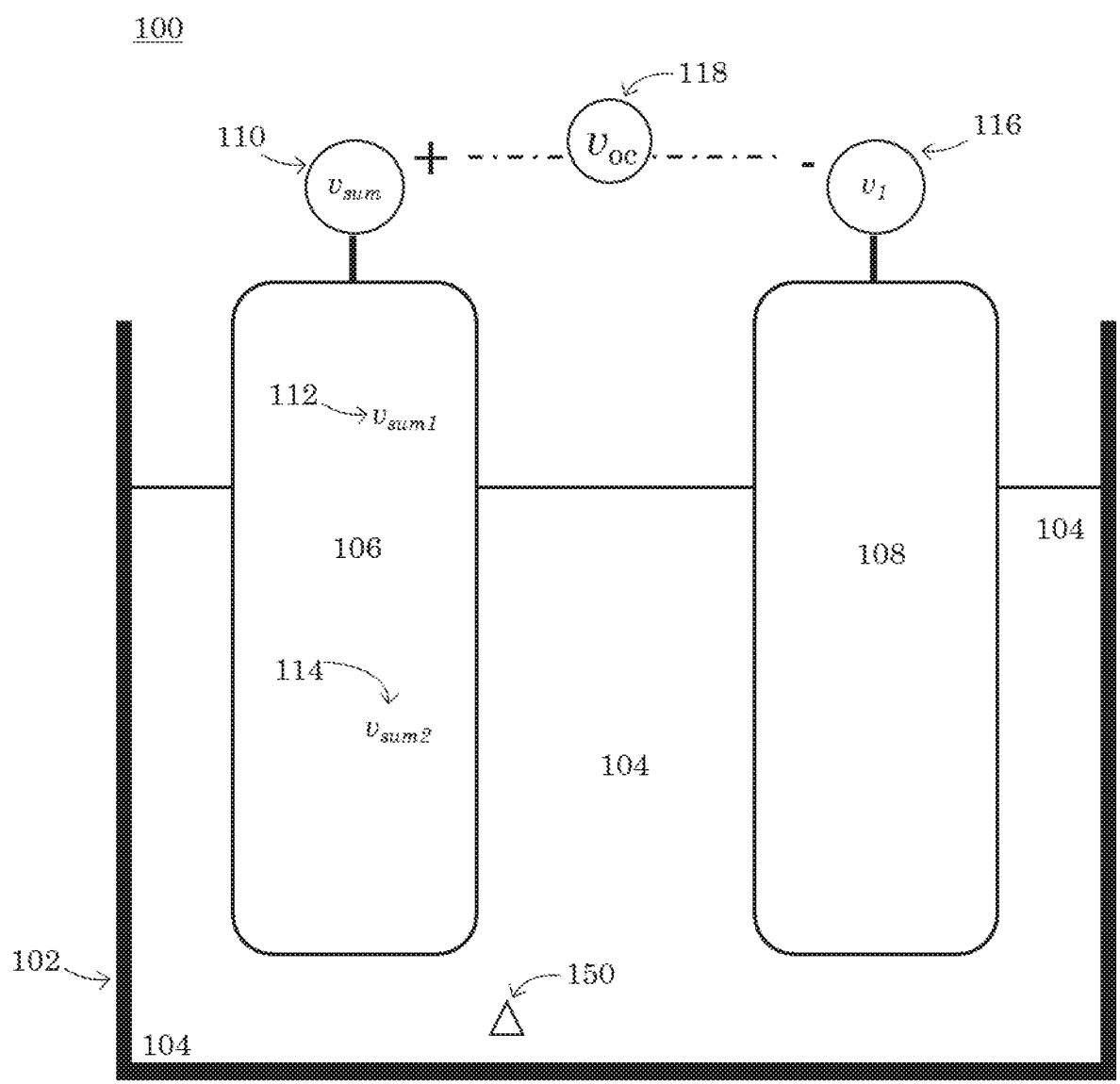
FIG. 1 is a sectional view of a first embodiment of a potentiometric sensor according to the invention.

Referring to FIG. 1, a sectional view of an embodiment of a potentiometric sensor 100 is shown. Within a vessel 102, there is a cathode 106 in communication with an anode 108 through a first electrolyte 104.

The vessel 102 can be any container capable of operably holding the potentiometric sensor 100. The vessel 102 is made from any material insoluble to and electrically insulated from the contents of the potentiometric sensor 100. For example, the vessel 102 can be made from alumina. Alumina, aluminum oxide, is an electrical insulator on its own and is insoluble to most electrolytes. The vessel 102 could also be made from stainless steel; stainless steel is electrically insulated from the potentiometric sensor 100 and is insoluble to most electrolytes. The internal diameter or width of the vessel 102 can be any size that is capable of housing the sensor. For example, it can be as small as 3 cm or as large as 100 cm.

The cathode 106 is ionically conductive and provides a summary voltage 110, $v_{sum}$. The cathode 106 does not degrade or react with the first electrolyte 104. The cathode 106 contains at least two voltage points within the cathode 106. As shown in FIG. 1, in this embodiment the at least two voltage points are represented by $v_{sum1}$ 112 and $v_{sum2}$ 114. The two voltage points, $v_{sum1}$ 112 and $v_{sum2}$ 114, are representative points in the cathode 106 a potential is created and are measurable. The voltage points create a summary voltage 110, $v_{sum}$. The at least two voltage points are distinct locations, though, in some embodiments their voltage values may be equal to one another. When more than two voltage points are used in different embodiments, each of the voltage points are where voltage is created. The at least two voltage points are voltages created through an ion exchange or ion transport processes within the cathode 106. The precise ion exchange or ion transport processes that create the at least two voltage points depends upon the composition of the cathode 106 and the first electrolyte 104. The two voltage points are dependent on the activity of the target ion 150. The summary voltage 110 may be constant or may fluctuate in response to the ion exchange process.

The anode 108 is electrically conductive and provides a first voltage 116. As shown in FIG. 1, in this embodiment the first voltage 116 is $v_1$. The anode 108 does not degrade or react to the first electrolyte 104. The first voltage 116 may be constant and does not change when the concentration of the target ion changes.

The summary voltage 110 and first voltage 116 can be measured in any way that accurately provides a measurement from which the voltage can be determined. For example, a high resistance voltmeter can be used. In some embodiments, an ammeter, ohmmeter, pressure sensor, flow sensor, capacitive sensor, acoustic sensor, optical sensor, or the like can be used to then derive the voltage measurement. A different or the same method of measuring voltage can lie used for measuring the summary voltage 110 and first voltage 116. In some embodiments, the voltage measurement at the voltage points can also be measured. The voltage measurements may be stored in a machine-readable medium.

The cathode 106 is in communication with the anode 108 by a first electrolyte 104, forming an open circuit that has an open circuit potential 118. The first electrolyte 104 has within it an unknown concentration of a target ion 150. The first electrolyte 104 is any electrically conducting solution in which ions are dissolved. The first electrolyte 104 may be at room temperature, but may also be at increased or decreased temperatures. For example, the first electrolyte 104 may be at 500° C.

The first electrolyte 104 is a solution and has within it an unknown concentration of a target ion 150. The concentration of the target ion 150 mathematically corresponds to the open circuit potential 118 created by the first voltage 116 of the anode 108 and the summary voltage 110 of the cathode 106. Because the open circuit potential 118 mathematically corresponds to the concentration of the target ion 150, knowing the open circuit potential 118 allows the concentration of the target ion 150 to be calculated. In some embodiments, the summary voltage 110 and first voltage 116 may also be used to calculate the concentration of the target ion 150. The open circuit potential 118 may be constant or may fluctuate. In an embodiment, the first electrolyte 104 is LiCl—KCl-xUCl$_3$ where x is the concentration of the target ion 150, the target ion 150 being UCl$_3$, and x can be determined by measuring the open circuit potential 118.

Prior art systems have relied on the measurement of open circuit potential of a system using a metal electrode as the anode, which is unable to provide a constant and accurate potential when the concentration of the ion to lie monitored within the first electrolyte 104 changes. The present invention uses an anode 108 that can provide a constant first voltage 116 independent of the ion to be monitored within the first electrolyte 104. The use of at least two voltage points in the cathode creates an accurate determination of the concentration of the target ion 150.

Prior art systems do not rely on multiple voltage points to determine the concentration of the target ion. Adding additional voltage points was not included in the prior art because it was not thought additional voltage points were necessary. Nor would it be possible to add additional voltage points because only one ion exchange or ion transport processes within the cathode, between an electrolyte within the cathode to the known electrolyte, was monitored. The present invention, which relies on at least two voltage points within the cathode renders more accurate determination of the concentration of the target ion due to the mathematical relationship between the voltage points and the target ion. The prior art does not lead to a general expectation of greater results because in the instant invention the mathematical relationship between the target ion and the open circuit voltage is more accurate when additional voltage points are used and when using an anode that is independent of the activity of the ion in the electrolyte 104.

Figure 2:
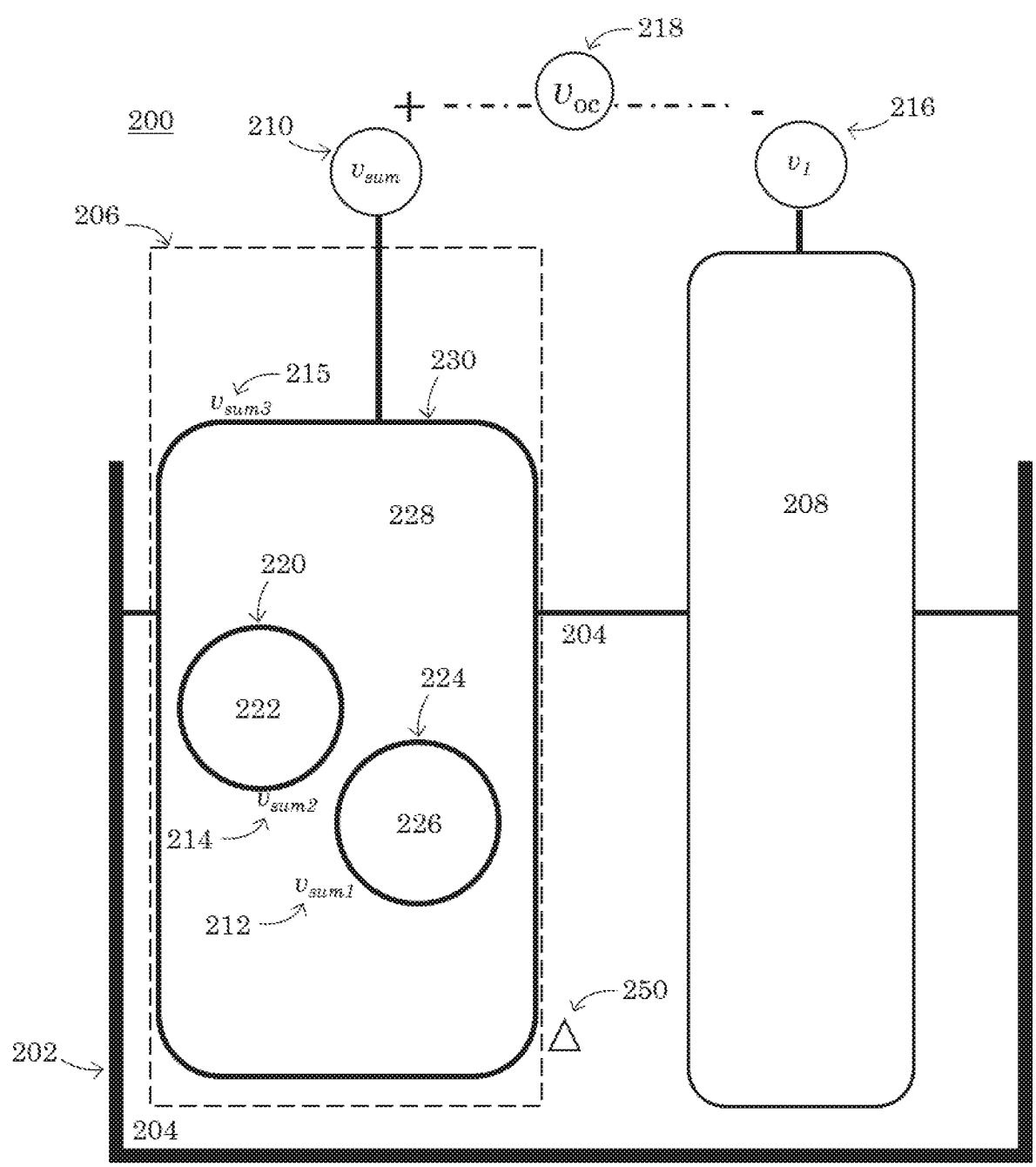
FIG. 2 is a sectional view of a second embodiment of a potentiometric sensor according to the invention.

The potentiometric sensor 200 in FIG. 2 includes basically the same configuration as that of the potentiometric sensor 100 in FIG. 1. Except, that within the vessel 202, in addition to the anode 208, the cathode 206 in the potentiometric sensor 200 in FIG. 2 has three voltage points: $v_{sum1}$ 212, $v_{sum2}$ 214, and $v_{sum3}$ 215. These voltage points are created from ion exchange or ion transport processes at the first membrane 224, second membrane 220, and third membrane 230. The membranes can be ion selective and have a high degree of selectivity. If the membrane is ion selective, the selectivity of the membrane is determined by the composition of the membrane and ideally allows the exchange of a specific ion or ions into it. The membrane excludes all ions except for the ion of interest. For example, the membrane can be selective for rare earth metals, and the ion of interest could be $Ce^{3+}$ or $Y^{3+}$. The membrane could also be selective for actinide ions including $U^{3+}$ and $Pu^{3+}$. The potential generated at the membrane, in response to the ion exchange or ion transport process through the membrane from one electrolyte to another, is generated only because that specific ion species migrates across the membrane. A potential will only be generated if there is more or less of the target ion species on one side of a membrane than the other side of the membrane. For example, there will only be a potential generated at the third voltage point, $v_{sum3}$, if there is more or less of the target ion species in the first electrolyte 204 than the second electrolyte 228.

The three voltage points together create the summary voltage 210, $v_{sum}$. The first voltage point, $v_{sum1}$ 212, is created through the ion exchange or ion transport processes occurring at a first membrane 224 containing a third electrolyte 226. The second voltage point, $v_{sum2}$ 214, is created through the ion exchange or ion transport processes occurring at a second membrane 220 containing a fourth electrolyte 222. The third voltage point, $v_{sum3}$ 215, is created through the ion exchange or ion transport processes occurring at a third membrane 230 containing a second electrolyte 228. Together, $v_{sum1}$ 212, $v_{sum2}$ 214, and $v_{sum3}$ 215, create the summary voltage 210, $v_{sum}$.

The first electrolyte 204 has within it an unknown concentration of a target ion 250. The open circuit potential 218 mathematically corresponds to the concentration of the target ion 250, and consequently, the open circuit potential 218 mathematically corresponds to the voltage points $v_{sum1}$ 212, $v_{sum2}$ 214, and $v_{sum3}$ 215. Using the open circuit potential 218, the first voltage 216, and the voltage points $v_{sum1}$ 212, $v_{sum2}$ 214, and $v_{sum3}$ 215, the target ion 250 can be determined. In an embodiment, the first electrolyte 204 is LiCl—KCl-xUCl$_3$ where x is the concentration of the target ion 250, the target ion 250 being UCl$_3$, and x corresponds logarithmically to the open circuit potential 218.

Figure 3:
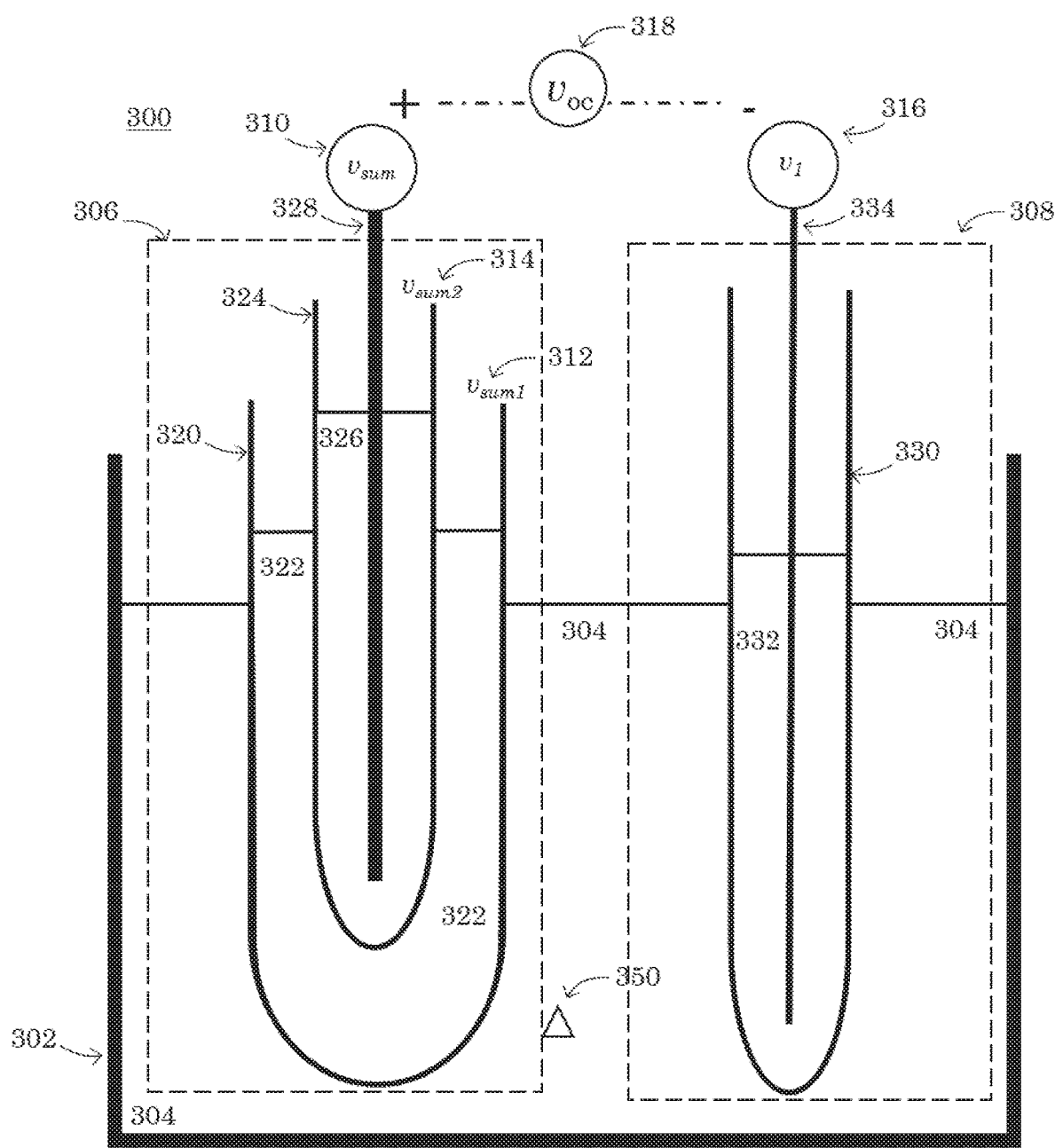
FIG. 3 is a sectional view of a third embodiment of a potentiometric sensor according to the invention.

FIG. 3 illustrates an embodiment of a potentiometric sensor 300, similar to the potentiometric sensors in FIG. 1 and FIG. 2. In FIG. 3, within a vessel 302, there is a cathode 306 in communication with an anode 308 through a first electrolyte 304. Within the cathode 306 is a first membrane 320 in communication with a second membrane 324 through a second electrolyte 322. The second membrane 324 is in communication with a first electrode 328 through a third electrolyte 326.

The first membrane 320 is a U-β" alumina membrane. The U-β" alumina membrane is $U^{3+}$ ion selective, which can be made by an ion exchange process from a Na-β" (or other) alumina membranes. The first membrane 320 can be made from more than one layer. For example, the first membrane 320 can have least two layers of materials, the first material including U-β" alumina, and the second material including at least one of: Na-, K-, or Sr-β" alumina. The first membrane 320 is ion selective and has a high degree of selectivity. The first membrane 320 allows the exchange of $U^{3+}$ ion or ions into it; therefore, the first membrane 320 excludes all ions except for $U^{3+}$ ion or ions. Therefore, the potential generated at the first membrane 320 is in response to the $U^{3+}$ ion exchange or $U^{3+}$ ion transport process through the first membrane 320 from the first electrolyte 302 to the second electrolyte 322.

The second membrane 324 and third membrane 330 can be made from the same or different materials. Different embodiments may require the second membrane 324 and third membrane 330 to have different material compositions. In this embodiment, the second membrane 324 and third membrane 330 are ceramic membranes, such as mullite membranes. Mullite is any of a type of rare mineral consisting of aluminum silicate ($3Al_2O_3 \cdot 2SiO_2$).

The second electrolyte 322, third electrolyte 326, and fourth electrolyte 332 have known electrolyte concentrations. The second electrolyte 322 can be LiCl—KCl salt containing a fixed amount of UCl$_3$. An example of salt composition can be LiCl—KCl-5 wt % UCl$_3$. The third electrolyte 326 and fourth electrolyte 332 are LiCl—KCl salt containing a fixed amount of AWL which corresponds to a fixed voltage. The composition of the third electrolyte 326 and the fourth electrolyte 332 can be the same or different.

The first electrode 328 and second electrode 334 are reference electrodes for molten chloride salts, for example, Ag/AgCl reference electrodes. The Ag/AgCl reference electrode consists of an Ag wire inserted in an electrolyte that is contained in an ion conductive thin-walled ceramic container, for example mullite.

The cathode 306 has two voltage points: $v_{sum1}$ 312 and $v_{sum2}$ 314. The voltage points together create the summary voltage 310, $v_{sum}$. One voltage point, $v_{sum1}$ 312, is created through the ion exchange or ion transport processes occurring at a first membrane 320. The second voltage point, $v_{sum2}$ 314, is created through the ion exchange or ion transport processes occurring at a second membrane 324. Together, $v_{sum1}$ 312 and $v_{sum2}$ 314 create the summary voltage 310, $v_{sum}$. The anode 308 has a first voltage, $\upsilon_1$, created through the electrode 334 and a third membrane 330.

The first electrolyte 304 has within it an unknown concentration of a target ion 350. The concentration of the target ion 350 mathematically corresponds to the open circuit potential 318 created by the first voltage 316 of the anode 308 and the summary voltage 310 of the cathode 306. Because the open circuit potential 318 mathematically corresponds to the concentration of the target ion 350, knowing the open circuit potential 318 allows the target ion 350 to be calculated. In an embodiment, the first electrolyte 304 is LiCl—KCl-xUCl$_3$ where x is the concentration of the target ion 350, the target ion 350 being UCl$_3$, and x can be determined by the measurement of open circuit potential 318. In some embodiments, the summary voltage 310 and first voltage 316 may also be used to calculate the concentration of the target ion 350. In some embodiments, the two voltage points, $v_{sum1}$ 312 and $v_{sum2}$ 314, may also be used to calculate the target ion 350. The open circuit potential 318 may be constant or may fluctuate.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

Any element in a claim that does not explicitly state "means for" performing a specified function, or "step for" performing a specific function, is not to be interpreted as a "means" or "step" clause as specified in 35 U.S.C. § 112, ¶6. In particular, the use of "step of" in the claims herein is not intended to invoke the provisions of 35 U.S.C. § 112, ¶6.

What is claimed is:

1. A potentiometric sensor comprising,
    (a) a cathode configured to provide a summary voltage representative of at least two voltage points;
    (b) an anode configured to provide a first voltage; and
    (c) the cathode in communication with the anode by a first electrolyte forming an open circuit, the first electrolyte including a concentration of a target ion, the target ion is UCl$_3$, the open circuit having an open circuit potential, wherein the open circuit potential mathematically corresponds to the concentration of the target ion.

2. The potentiometric sensor of claim 1 wherein the first electrolyte is a chloride salt.

3. The potentiometric sensor of claim 1 wherein the open circuit potential is logarithmically related to the target ion.

4. The potentiometric sensor of claim 1 wherein the cathode further comprises:
    (a) a first membrane having a first voltage point;
    (b) a second membrane having a second voltage point;
    (c) the first membrane in communication with the second membrane by a second electrolyte; and
    (d) a first electrode in communication with the second membrane by a third electrolyte.

5. The potentiometric sensor of claim 4 wherein the first electrolyte is LiCl—KCl—UCl$_3$.

6. The potentiometric sensor of claim 4 wherein the first membrane is selective for U$^{3+}$ ions.

7. The potentiometric sensor of 5 wherein the second electrolyte is LiCl—KCl salt.

8. The potentiometric sensor of claim 4 wherein the first membrane includes U-β" alumina.

9. The potentiometric sensor of claim 4 wherein the first membrane is made from at least two layers of materials, the first material including U-β" alumina, and the second material including at least one of: Na-, K-, or Sr-β" alumina.

10. The potentiometric sensor of claim 4 wherein the second membrane is a ceramic membrane.

11. The potentiometric sensor of claim 4 wherein the first electrode is a reference electrode for molten chloride salts.

12. The potentiometric sensor of claim 4 wherein the third electrolyte is a LiCl—KCl salt.

13. The potentiometric sensor of claim 1 wherein the anode further comprises:
    (a) a third membrane in communication with a second electrode by a fourth electrolyte.

14. The potentiometric sensor of claim 13 wherein the second electrode is a reference electrode for molten chloride salts.

15. The potentiometric sensor of claim 13 wherein the fourth electrolyte is LiCl—KCl salt.

16. The potentiometric sensor of claim 13 wherein the third membrane is a ceramic membrane.

* * * * *